United States Patent [19]

Coes

[11] Patent Number: 4,995,875
[45] Date of Patent: Feb. 26, 1991

[54] FEMORAL ELEVATING TOOL

[76] Inventor: Cecil Coes, 6830 Elwynn Dr., Cincinnati, Ohio 45236

[21] Appl. No.: 199,475

[22] Filed: May 27, 1988

[51] Int. Cl.[5] .................................................. A61F 2/00
[52] U.S. Cl. .......................................... 606/90; 606/99; 128/20
[58] Field of Search ...................... 128/20, 92 R, 92 V, 128/92 VT, 92 VY, 303 R; 623/18, 22, 23; 81/176.2, 94, 98; 606/53, 99, 82, 87, 88, 90

[56] References Cited

U.S. PATENT DOCUMENTS

| | | | |
|---|---|---|---|
| 1,474,497 | 11/1923 | Stolper | 128/20 |
| 2,695,607 | 11/1954 | Hipps et al. | 128/20 |
| 2,863,444 | 12/1958 | Winsten | 128/303 R |
| 3,381,685 | 5/1968 | Von Solbrig | 128/92 VT |
| 3,463,144 | 8/1969 | Hammond | 128/20 |
| 3,467,079 | 9/1969 | James | 128/20 |
| 3,955,568 | 5/1976 | Neufeld | 128/92 VT |
| 4,222,382 | 9/1980 | Antonsson et al. | 128/303 |
| 4,621,619 | 11/1986 | Sharpe | 129/20 |
| 4,632,111 | 12/1986 | Roche | 128/303 |
| 4,642,121 | 2/1987 | Keller | 623/23 |
| 4,686,972 | 8/1987 | Kurland | 128/92 |

OTHER PUBLICATIONS

Richards Reconstructive Systems "Modular Spectron—Design Features and Surgical Technique", Sep., 1986.

Primary Examiner—Robert A. Hafer
Assistant Examiner—Michael Brown
Attorney, Agent, or Firm—Frost & Jacobs

[57] ABSTRACT

A femoral elevating tool for use in hip replacement surgical procedures and preferably including a handle having a longitudinal axis and proximal and distal ends substantially parallel to one another. The proximal and distal ends are preferably offset from one another in a direction normal to the longitudinal axis by a central handle portion. A bone rest adjacent the distal end of the handle preferably includes an upstanding flange having a single, generally V-shaped cutout portion, and a ball for rotatably anchoring the tool in an acetabulum to provide a fulcrum for manipulation of a femur. In a preferred embodiment, the ball is adjustably mounted on the handle to enable selective variation of the effective distance between the ball and the bone rest, and the ball can be removed for cleaning and replacement with a different ball, as appropriate.

19 Claims, 4 Drawing Sheets

FEMORAL ELEVATING TOOL

TECHNICAL FIELD

This invention relates to an elevating tool for use in hip replacement surgical procedures, and, more particularly, to an improved femoral elevating tool which, in use, is anchored in an acetabulum to provide a fulcrum for atraumatically manipulating the upper portions of the femur during hip replacement surgical procedures.

BACKGROUND ART

Hip replacement arthroplasty has become widely accepted and has been remarkably successful as a procedure for relieving pain and restoring motion in patients suffering from disabilities resulting from various hip arthropathy. Generally, conversion endoprosthesis or total hip replacement prosthesis is often indicated for hip arthropathies involving the femoral side. For example, hip prosthesis is indicated in cases of degenerative joint disease from various causes, rhumatoid arthritis, and traumatic arthritis.

As part of total hip replacement surgery, the hip joint must be dislocated, and the femoral head must be lifted out of the acetabulum and brought out of the deep wound for further preparation and implant procedures. For example, the femoral neck must be transected, the medullary canal must be opened along the transected neck using a reamer or hollow chisel, and the medullary canal must be plugged. Thereafter, the medullary canal is cleaned and irrigated, there is a trial fitting of the femoral prosthesis, and femoral cement is filled and compressed within the medullary canal. Thereafter, the femoral stem is inserted and properly fitted in place. Because of the plug within the medullary canal and the compression of the cement, the force needed to insert the stem is relatively high, and pressure must be maintained until the cement is completely hardened. Throughout all of these procedures, the femur and the femoral neck must be manipulated and supported substantially outside of the deep wound. Heretofore, various bone retractors and femoral elevators available in the industry have been utilized to accomplish the support and manipulation of the femur required. Such bone retractors and femoral elevators previously available often required manipulative interaction with soft tissue adjacent the femur or femoral neck being manipulated and supported. In order to accomplish that manipulation and support, these devices generally depended upon leverage gained by support from those adjacent soft tissue structures. As a result, the soft tissue was often subjected to undue trauma and/or injury during these surgical procedures, and support provided by these instruments was inconsistent and unreliable.

For example, the self-retaining bone retractor shown in U.S. Pat. No. 2,695,607, which issued to H. Hipps et al., on Nov. 30, 1954, clearly shows the direct compression of soft tissue adjacent the bone and incision, and further contemplates utilization of a flexible connector wrapped around the external portions of that same soft tissue. Similar bone retractors are often utilized to manipulate and elevate the femur during hip replacement surgical procedures. Obviously, it is preferred during any surgical procedure to minimize undue trauma and injury whenever possible. The compressive forces imposed upon the soft tissue adjacent the bone as a result of utilizing the Hipps et al. bone retractor has heretofore been an undesirable necessity.

Another form of retractor commonly available in the industry and often used in hip replacement surgical procedures is the femoral neck elevator such as available from the Richards Medical Company of Memphis, Tenn. (e.g. Cat. No. 11-9674). Such femoral neck elevator, however, similarly relies on surrounding soft tissue for leverage in order to manipulate and support the femur and/or femoral neck. Its generally curved and multi-toothed bone rest portion also permits unpredictable slippage of the femur during manipulation and support procedures, making this instrument harder to work with. Consequently, while these instruments have been specifically designed for use in elevating the femur during hip replacement surgical procedures, their use fails to provide reliable support and can cause additional and often unnecessary trauma and/or injury to the surrounding soft tissue. While the overall damage of this additional trauma and/or injury may be outweighed by the overall benefit of the surgery to the patient, it would be preferable to provide an instrument which could minimize this undue trauma and injury while providing dependable and convenient femoral support and manipulation.

DISCLOSURE OF THE INVENTION

It is an object of the present invention to obviate the above-described problems.

It is also an object of the present invention to provide an improved femoral elevating tool for hip replacement surgical procedures which minimizes undue trauma and/or injury and provides manipulation and support of the femur during such procedures.

It is a further object of the present invention to provide an improved femoral elevating tool which includes a ball member for anchoring the tool in an acetabulum to provide a fulcrum for atraumatically manipulating and supporting a femur during surgical procedures.

It is another object of the present invention to provide a femoral elevating tool having a ball member and a bone rest member, wherein the longitudinal distance between the ball member and the bone rest can be adjusted for optimal performance in a variety of surgical applications.

In accordance with one aspect of the present invention, there is provided a femoral elevating tool for use in hip replacement surgical procedures and comprising a handle having proximal and distal ends and a longitudinal axis along its length. The handle includes a bone rest adjacent its distal end, and ball means attached to the handle for anchoring the tool in an acetabulum to provide a fulcrum for the tool. Means are also provided for adjusting the longitudinal distance along the handle between the ball means and the bone rest.

BRIEF DESCRIPTION OF THE DRAWINGS

While the specification concludes with claims particularly pointing out and distinctly claiming the present invention, it is believed that the same will be better understood from the following description taken in conjunction with the accompanying drawings in which:

DETAILED DESCRIPTION OF THE INVENTION

Referring now to the drawings in detail, wherein like numerals indicate the same elements throughout the views, there is illustrated a preferred embodiment of a femoral elevating tool made in conjunction with the subject invention, as well as various alternative embodiments and optional features. FIGS. 1-4 illustrate a preferred embodiment of a femoral elevating tool 10 made in accordance with the subject invention including a handle 20 having a proximal end 21 and a distal end 22. As seen best in FIG. 4, handle 20 includes a longitudinal axis A along which the proximal and distal ends 21 and 22, respectively, are most preferably aligned. It is not critical to the elevating tool of the subject invention that the proximal and distal ends of the tool be symmetric with or coaxially aligned with longitudinal axis A, although in a preferred embodiment they are.

Figures 2, 3:
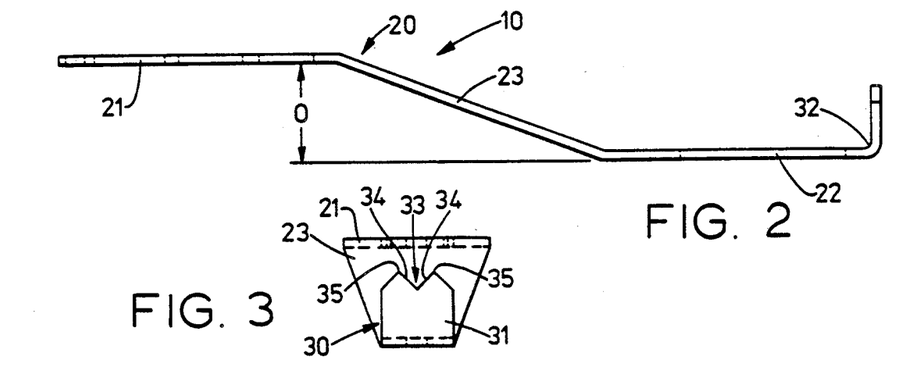
FIG. 2 is front elevational view of the handle portion of the elevating tool of FIG. 1.
FIG. 3 is a right side view of the handle shown in FIG. 2.

As seen best in FIG. 2, handle 20 can feature a relatively thin, ribbon-like profile of substantially uniform thickness. In this regard, because the femoral elevating tool of the subject invention is contemplated for repeated use in hip replacement surgical procedures, it is critical that the material from which tool 10 is made be strong enough to withstand the relatively high shearing, twisting and similar forces which will be imposed during its use, as will be described in greater detail below. While it is quite conceivable that the femoral elevating tool 10 could indeed be made of high strength plastic or similar materials for disposable use, it is preferred that elevating tool 10 be formed of autoclavable steel alloy or similar materials. In this regard, it is commonly understood that reusable surgical implements and tools must be carefully sterilized between uses for protection of both the patient and the medical workers using and handling the instrument. It is further preferred that the material from which elevating tool 10 is formed be ebonized (or appropriately colored and/or finished) in order to minimize reflection of light which could impair the vision of the surgeon or his assistants during surgical procedures.

Figure 1:
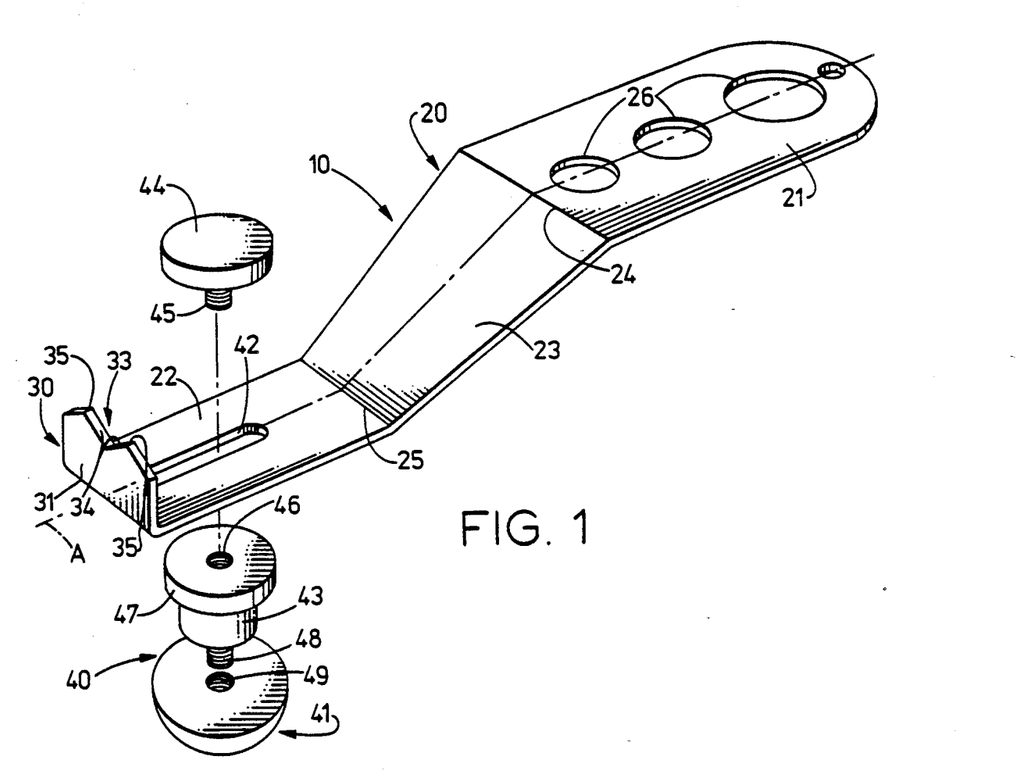
FIG. 1 is a partially exploded, perspective view of a preferred embodiment of a femoral elevating tool made in accordance with the subject invention.

Handle 20 is further shown as including a bone rest structure 30 adjacent its distal end 22. In particular, as will be described in greater detail below, the bone rest 30 is a portion of the elevating tool 10 which will be situated beneath the neck portion of a femur in use in order to manipulate and support the femur during various surgical procedures. Bone rest 30 further comprises an upstanding flange 31 connected adjacent the distal-most portion of handle 20 along line of attachment 32. Means (e.g. cutout 33) are provided in the upper portion of upstanding flange 31 for accommodating the neck portion of a femur to be supported. While any of a variety of concave cutout configurations for cutout 33 could be utilized adjacent the upper edge of upstanding flange 31, it is preferred that a single, generally V-shaped, tapered cut out portion 33 be formed in the upper-most portions of flange 31 to provide a slip-resistant support arrangement. The V-shape of cutout 33 provides a bone rest support structure which can accommodate a relatively wide range of bone sizes while minimizing the potential for lateral movement or slippage of the bone therewithin. While prior art retractors commonly used for hip replacement surgical procedures often include generally rounded cutout portions having a plurality of triangular teeth formed therewithin, the single V-shape feature of the bone rest described herein prevents the tendency of the bone to shift laterally within the bone rest cutout during manipulation and support procedures. A bone being supported within bone rest 30 tends to nest within cutout 33, with the oppositely slanted surfaces 34 thereof tending to hold the bone motionless therewithin. The single V-shape thereby provides a more reliable and steady support between the oppositely disposed bone confinement ridges 35.

Proximal end 21 of handle 10 is preferably integrally connected to distal end 22 by central handle portion 23. As seen best in FIGS. 1 and 4, proximal end 21 is connected to central handle portion 23 along attachment line or intersection 24, while distal end 22 is connected to central handle portion 23 along attachment line or intersection 25. It is further contemplated that it may be preferable to form handle 20 of a single, substantially flat piece of steel or alloy, first cutting the flat sheet to the shape preferred, and, thereafter, bending handle 20 as desired to provide the proximal, central handle, and distal portions thereof, as shown. As can be seen in FIGS. 1 and 2, it is further preferable to connect proximal end 21 and distal end 22 in such a way as to provide a vertical offset O therebetween. In order to provide the offset O, it is further preferred to angularly orient central handle portion 23 to proximal end 21 and distal end 22, respectively. It has been observed that providing a slight offset between the proximal end 21 of handle 20 and distal end 22 will facilitate manipulation of tool 10 in use and can provide greater leverage for the surgeon.

Femoral elevating tool 10 further comprises ball means 40 attached to handle 20 for anchoring the tool in an acetabulum during hip replacement surgical procedures to provide a fulcrum for tool 10. Preferably, such ball means 40 further includes a generally hemispherical element or ball 41 designed for rotatable interaction with an acetabulum to provide a fulcrum for tool 10 independent of surrounding soft tissue of the patient. Means are further preferably provided for adjusting the longitudinal distance along handle 20 between ball means 40 and bone rest 30. In a most preferred embodiment, and as illustrated in the exploded view of FIG. 1, such means for adjusting the longitudinal distance between ball means 40 and bone rest 30 comprises an adjustable mount arrangement for ball means 40, whereby ball means 40 can be selectively secured at a desired position along handle 20 relative bone rest 30.

As shown in FIG. 1, a preferred way of providing for longitudinal adjustment of ball means 40 along handle 20 includes the provision of a longitudinal adjusting slot 42 in distal end 22 along which ball means 40 can be selectively secured. In particular, it is contemplated that hemispherical ball element 41 can be attached along adjustment slot 42 by threaded interaction between knob 44 and ball standoff 43. To facilitate such adjustment, it is contemplated that ball standoff 43 can be provided with an enlarged disk-like portion 47 having a threaded bore 46 formed therein for threaded interaction with threaded shank 45 attached to knob 44. Knurling or similar surface finish can also be provided on knob 44 and portion 47 to facilitate digital manipulation by the user. By loosening the threaded connection between knob 44 and ball standoff 43, ball means 40 can be slidably adjusted along adjustment slot 42. Ball standoff 43 provides adjustable attachment of hemispherical ball element 41, and further spaces ball element 41 somewhat from handle 20 in a direction perpendicular to longitudinal axis A to enable a wider range of rotatable interaction between ball means 40 and the acetabulum of the patient.

Figure 9:
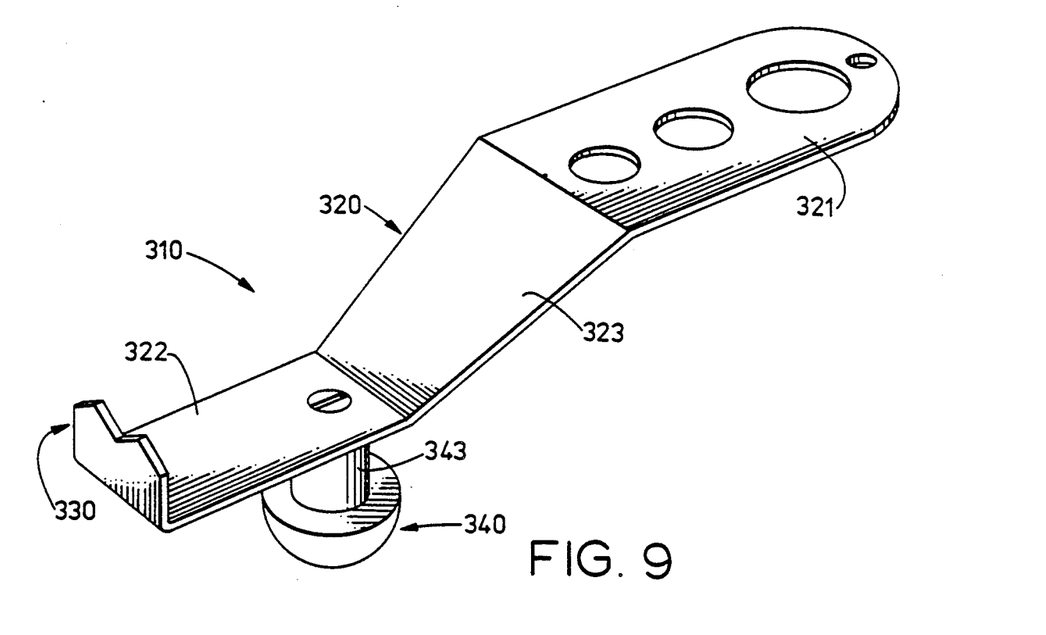
FIG. 9 is a perspective view of yet another alternate and simpler embodiment of a femoral elevating tool of the subject invention.

By providing means for adjusting the longitudinal distance along handle 20 between ball means 40 and bone rest 30, elevating tool 10 can be adjusted in any particular surgical procedure to adapt to the relatively limitless variation of bone sizes and hip replacement applications encountered by the surgeon. For example, for optimal performance of tool 10, different bone sizes and overall size variations between patients require corresponding variation between the ball means anchored in an acetabulum and the bone rest situated below the neck of the femur to be supported. Moreover, depending upon exactly where the neck of the femur is transected, the distance between the acetabulum and the transected femur will vary between particular surgical procedures. Adjustability of the longitudinal distance between ball means 40 and bone rest 30 enables a single elevating tool 10 to be adaptable in order to more precisely meet the particular needs of each procedure. It should be noted, however, that it is contemplated that the simplest form of the subject elevating tool could adequately provide some of the benefits discussed herein without including means to adjust the longitudinal distance between the ball and the bone rest. Such an embodiment would be as illustrated in FIG. 9, wherein ball standoff 343 is non-adjustably attached to distal end 322 at a predetermined distance from bone rest 330.

Figure 4:
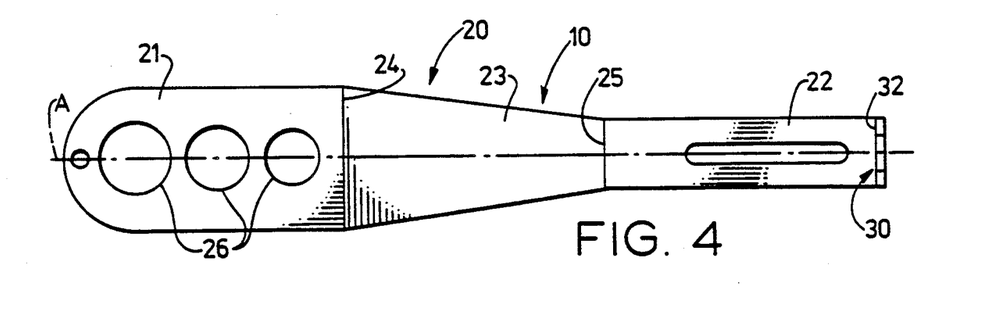
FIG. 4 is a top plan view of the handle of FIG. 2.

As best shown in FIG. 4, the proximal end 21 of handle 20 preferably includes one or more cooling cutouts or holes 26 provided to facilitate the autoclaving of sterilization process of tool 10 between uses. Such cooling holes are commonly provided in surgical instruments requiring high temperature sterilization or autoclaving. The exact number, shape, and location of such cooling holes is not critical and can be selected as appropriate.

FIG. 1 further illustrates hemispherical ball element 41 as being detachably connected to ball standoff 43 by the provision of the threaded standoff shank 48 and the corresponding threaded bore 49 formed within ball element 41. In this regard, it is preferred to provide for the removal and replacement of ball 41 in order to facilitate cleaning and storage of tool 10, as well as to enable the replacement of ball 41 with other ball elements of various size and/or shape. In this regard, it is not critical that ball 41 be precisely hemispherical in shape, and it is recognized that particular acetabulums will have unique sizes, depths, and shapes. It is contemplated that tool 10 could be provided with a variety of ball structures 41 to provide the surgeon with the ability to in effect "customize" ball means 40 of tool 10 to best correspond with the circumstances of the particular surgical application. For example, a ball element 41 having a larger effective diameter might be required for a generally larger patient, while another ball element 41 of particular size and/or shape might be preferred for a smaller acetabulum having a deeper concavity within which the tool is to be anchored. In this regard, it is understood that often the patient's acetabulum is diseased and may provide a less than optimal socket for insertion of ball means 40. By providing a relatively wide variety of shapes and sizes of ball elements 41 for a particular tool 10, the surgeon may still be able to utilize whatever parts of a particular acetabulum are available to anchor the tool and to provide a fulcrum for manipulation of the femur independent of support by other soft tissues and the like which can easily be damaged. It should be noted that the threaded interaction of the various parts of the subject tool 10 to provide selective adjustability along and removability from handle 20 are shown and described only as a preferred combination of interacting elements. The exact manner of providing such adjustability and removable attachment is not critical to the subject invention and can be accomplished by other structures known in the industry or adaptable to this structure by one knowledgable in art.

Figure 7:
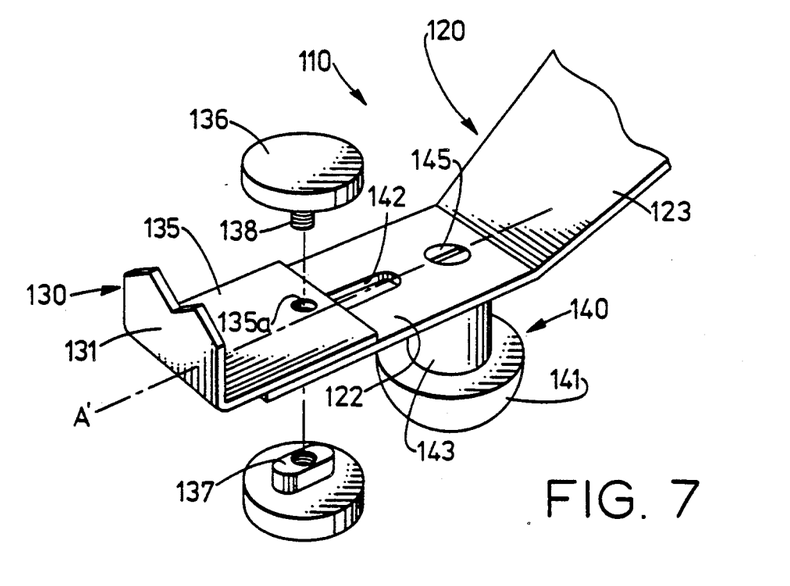
FIG. 7 is a partial, perspective view of an alternate embodiment of a femoral elevating tool made in accordance with the subject invention.

In this regard, FIG. 7 is a partial perspective view of a handle 120 of an alternate embodiment of a femoral elevating tool 110 made in accordance with the subject invention. In particular, it is contemplated that the means for adjusting the longitudinal distance along the handle 120 between ball means 140 and bone rest 130 of a femoral elevating tool 110 made in accordance with the subject invention could also comprise an adjustable mount arrangement of the bone rest 130 relative a substantially stationary ball means 140. FIG. 7 shows ball means 140 including a standoff 143 non-adjustably mounted (i.e. by screw 145), and wherein bone rest 130 can be selectively attached along handle 120 at a desirable distance from ball means 140. The adjustable mount arrangement for bone rest 130 comprises a telescopic extension 135 of bone rest flange 131 which enables the selective securement of bone rest 130 along handle 120 by appropriate tightening and loosening of knob 136 relative oppositely disposed nut 137. In this regard, knob 136 would preferably include a depending threaded shank 130 passing through bore 135a of telescopic extension 135, adjustment slot 142, and threadedly received within captive nut 137. By loosening knob 136, the telescopic sleeve 135 and the attached bone rest 130 can be adjusted longitudinally along longitudinal axis A' to thereby adjust the longitudinal distance along handle 120 between bone rest 130 and ball means 140.

Figure 8:
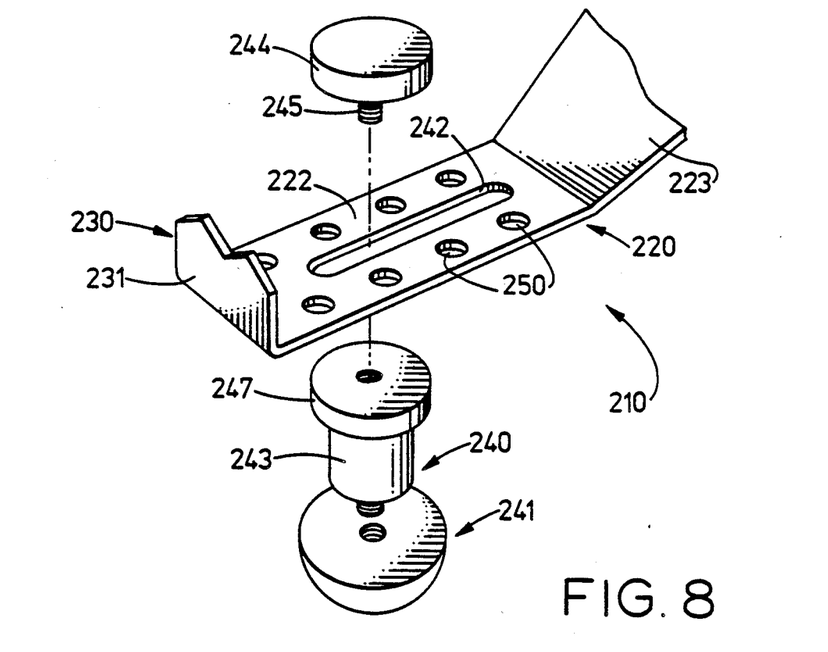
FIG. 8 is a partial, exploded view of another alternate embodiment of a femoral elevating tool of the subject invention.

FIG. 8 illustrates yet a further embodiment of a femoral elevating tool 210 made in accordance with the subject invention. The embodiment shown in FIG. 8 is substantially similar to the embodiment shown and described with regard to FIG. 1, with the addition of a plurality of offset ball means mounting holes 250 arranged at predetermined positions along distal end 222. It is contemplated that the ball means mounting holes 250 might be desirable to provide additional predetermined adjustment of ball means 240 relative bone rest 230 in order to provide both longitudinal and lateral adjustment of ball means 240. In this regard, it is contemplated that in some applications of the elevating tool of the subject invention, it may be further advantageous to provide lateral adjustment between the ball means and bone rest structures of the tool to provide further enhanced leverage of the tool, and/or to facilitate the support and manipulation of a femur during hip replacement surgical procedures. By providing this additional lateral adjustment capability, a surgeon skilled in the use of the elevating tool of the subject invention could obtain additional leverage and/or the ability to better position the elevating tool and/or the femur during particular surgical procedures.

For example, by offsetting the ball means 240, a surgeon may be able to ensure that the elevating tool 210 does not interfere with access to the deep wound during preparation, trial fitting, or inserting the femoral prosthesis and the like. The number and location of these auxiliary mounting holes 250 can be specifically designed and labeled to optimize these features and to facilitate their use by surgeons. It is further contemplated that adjustment slot 242 could be used with these auxiliary holes 250, or omitted. Similarly, adjustment slot 242 might be replaced by a plurality of longitudinally spaced mounting holes similar to holes 250. Likewise, a series of laterally spaced longitudinal slots (not shown) could also be utilized to provide infinite longitudinal adjustment along various laterally spaced slots. Of course, it must be kept in mind that such slots 242 and auxiliary holes 250 tend to weaken the handle of the elevating tool, and the number and location of such slots and/or holes must be considered in light of other characteristics of the tool, such as required strength and the like. For example, if more adjustability was desired, more holes and/or slots might require the use of a stronger or thicker material. To minimize thickness of such tool, a stronger alloy might also be implemented, as appropriate.

As set forth above, the femoral elevating tool shown and described herein provides a unique apparatus which can be adjusted for use in a relatively limitless variety of hip replacement surgical applications, and which provides for dependable and steady support and manipulation of a femur during such surgical procedures in a way which is substantially atraumatic to soft tissue of the patient. As will be set forth below, by providing a ball means for anchoring the tool in an acetabulum to provide a fulcrum for the tool in use, a femoral elevating tool of the subject invention is anatomically functional with the patient's acetabulum and simulates the natural ball socket movement and manipulation to prevent undue trauma to soft tissues adjacent the patient's hip.

Figure 5:
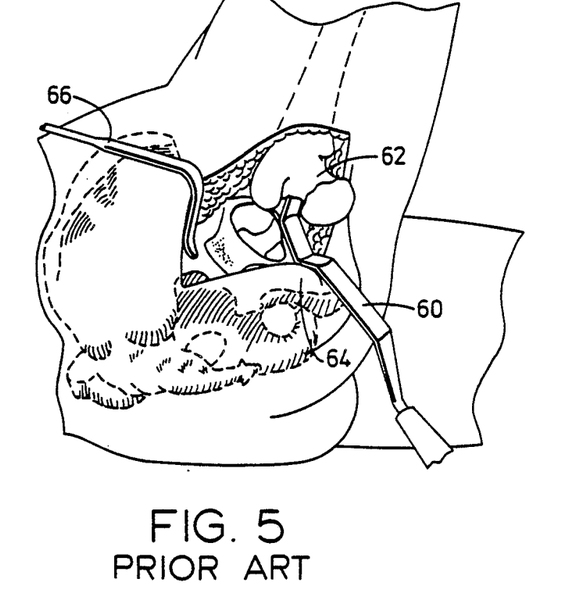
FIG. 5 is a partial, schematic view of a prior art femoral neck elevator device being used to support a femoral neck in a surgical operation where the hip joint has been adducted and externally rotated.

FIG. 5 illustrates a partial schematic view of the use of a prior art femoral neck retractor or elevator tool 60 commonly implemented during hip replacement surgical procedures. In particular, FIG. 5 shows a typical retractor 60 being utilized to support and manipulate a femoral neck 62 within an incision. FIG. 5 also shows the use of a common retractor 66 to retract tissue adjacent the incision. It should be noted that in order to provide support for femoral neck 62, the prior art femoral elevator or retractor 60 necessarily relies upon the surrounding soft tissue 64 of the patient. In this regard, it is easily understood that such support by surrounding soft tissue 64 necessarily results in inconsistent and unreliable support as well as in varying degrees of trauma and/or damage to such soft tissue. Moreover, as described above, such prior art retractors or femoral elevators feature a generally circular, concave bone rest portion having a plurality of triangular tooth-shaped supports which often allow lateral slippage of the femur and femoral neck during bone manipulation and/or prosthesis preparation and insertion procedures. As a result, the femoral neck being supported often slips within the support of the retractor device, resulting in unreliable support and, often, a need to reposition the retractor for better support. Such repositioning necessarily causes additional trauma to the soft tissue upon the which the retractor was supported.

Figure 6:
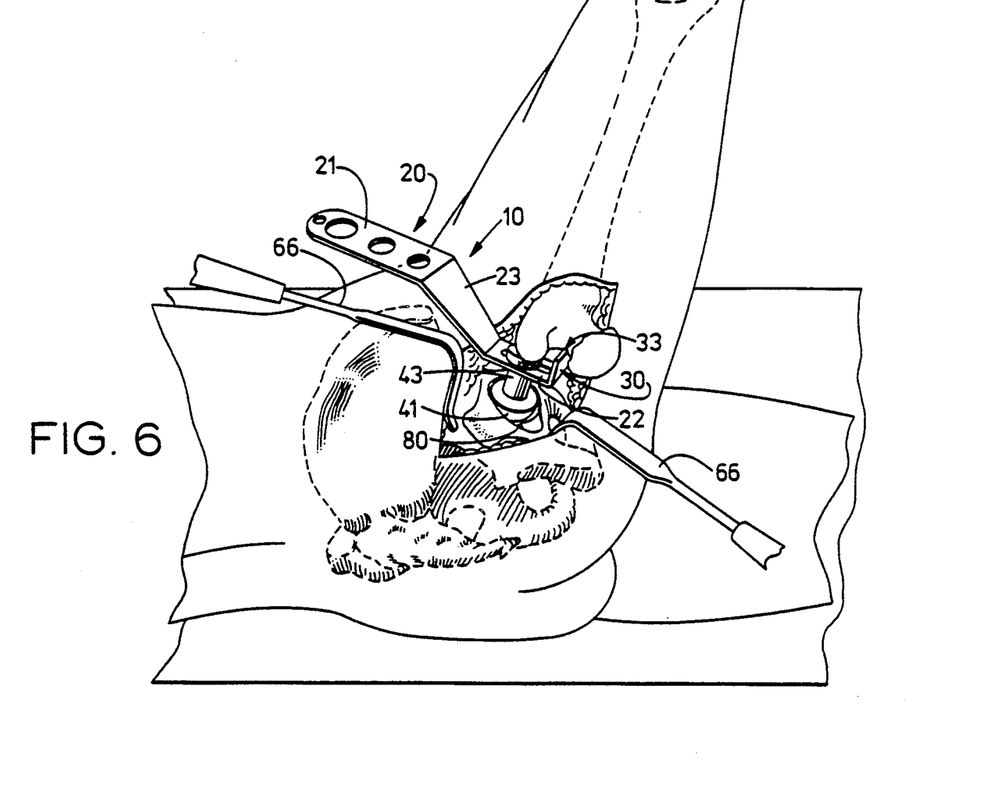
FIG. 6 is a partial, schematic view similar to the view of FIG. 5, showing the use of the femoral elevating tool of the instant invention in a hip replacement procedure wherein the ball member of the tool is anchored in the acetabulum and the bone rest is below and supporting a femoral neck of the patient.

Looking closer at the use of the femoral elevating tool 10 of the subject invention, the perineal area of the patient is to be sealed off with a plastic drape or the like after the patient has been placed in a lateral recumbant position for surgery. The leg is widely adducted and the skin prepared below the rib cage to the knee. After the initial incision has been completed, the thigh is rotated internally to expose the posterior aspect of the hip in order to begin capsulectomy. After the hip has been dislocated, the hip is flexed and adducted to deliver the femoral head out of the incision. The leg is then rotated such that the femoral head is pointing superiorly. At this point, the bone rest 30 of femoral elevating tool 10 can be carefully inserted into the deep wound below the femoral head to support the neck portion of the femur. Insertion of elevating tool 10 is preferably undertaken with the upstanding flange 31 facing upwardly such that ball element 41 can be fitted within the acetabulum 80 of the patient (see FIG. 6). FIG. 6 also shows the use of common retractors 66 to retract surrounding soft tissue during surgical procedures. Once ball element 41 is inserted into the patient's acetabulum 80, it will provide an anchor for tool 10 within the acetabulum to provide a fulcrum for the tool independent of the surrounding soft tissue. Insertion of ball element 41 into the natural acetabulum 80 of the patient provides a relatively solid and reliable support arrangement for tool 10. By supporting the femur below its neck within the single, V-shaped tapered cutout portion 33, the surgeon can support and manipulate the distal end of the femur by utilization of elevating tool 10 as a lever. The surgeon will grasp tool 10 at the proximal end 21 of handle 20, and will enjoy the mechanical advantage provided by the lever/fulcrum interaction of tool 10 with the acetabulum 80 of the patient without reliance on soft tissue for support. Once the femur has been supported within bone rest 30, it can be reliably held during transection of the femoral neck, femoral preparation, femoral prosthesis trial fitting and insertion, femoral head impact locking, and other similar procedures.

For example, the medullary canal of the transected neck must be commonly opened during femoral preparation utlizing a reamer, hollow chisel, or rasp. During trial fitting of the femoral prosthesis, the hip must be reduced for confirming correct length of the prosthesis and to ensure that sufficient anteversion in the prosthesis in the medullary canal is provided. Similarly, the canal must be plugged and cleaned, and femoral cement must be compressed therewithin prior to fixation of the femoral stem. It must be kept in mind that substantial force is needed to compress the femoral cement and to insert the stem, and reliable and steady support of the femoral neck is critical throughout these procedures. The femoral elevating tool of the subject invention provides enhanced support, steadiness, and reliability, along with unprecedented adjustability, while at the same time eliminating and minimizing undue trauma to surrounding soft tissues. It must be kept in mind that dislocations, subluxation, decreased range of motion, and lengthening or shortening of the femur are some of the adverse effects often caused by improper positioning or looseness of femoral components, and penetration of the femoral stem through the shaft of the femur can also result from improper reaming of the medullary canal. By providing a more reliable and steady support for the femur, the potential for these various complications can be reduced. Moreover, these additional benefits are obtained while simultaneously obviating undue trauma to surrounding soft tissue. The rotatable interaction of ball means 40 of the tool 10 described herein provides a wide range of motion of the tool facilitating overall manipulation of the femur. In conjunction with manipulation by the surgeon's assistant of the patient's leg, proper use of the subject invention can substantially reduce operative stresses on the various tissues, as well as the bones involved. By minimizing such stresses and undue trauma to the various soft tissues, post-operative recovery and rehabilitation can also be accelerated.

The foregoing description of the preferred embodiments of the invention have been presented for purposes of illustration and description. Accordingly, this is not intended to be exhaustive or to limit the invention to the precise form disclosed, and obviously many modifications and variations are possible in light of the above teachings. Several of such modifications or variations have been described herein, and additional modifications will be apparent and can be accomplished by those skilled in the art. Accordingly, the scope of the present invention should be considered in terms of the following claims and is understood not to be limited to the details of the structures shown and described in the specification and drawings.

I claim:

1. A femoral elevating tool for use in hip replacement surgical procedures, said tool comprising a handle having proximal and distal ends and a longitudinal axis along its length, said handle including a bone rest adjacent its distal end and being substantially planar to its perpendicular axis, and a ball means attached to said handle intermediate said proximal and distal ends and extending outwardly from said longitudinal axis for anchoring said tool in an acetabulum to provide a fulcrum for said tool.

2. The femoral elevating tool of claim 1, further comprising means for adjusting the longitudinal distance along said handle between said ball means and said bone rest.

3. The femoral elevating tool of claim 1, wherein said bone rest further comprises a flange portion extending upwardly from said handle, said flange portion including a single, generally V-shaped tapered cutout portion on its distal end to provide a slip-resistant support for a bone to be elevated.

4. A femoral elevating tool for use in hip replacement surgical procedures, said tool comprising a handle having proximal and distal ends along a longitudinal axis thereof, said handle including a bone rest adjacent its distal end, and ball means adjustably attached to said handle for anchoring said tool in an acetabulum to provide a fulcrum for said tool, said ball means being adjustable along the longitudinal axis to selectively vary the effective distance between said ball means and said bone rest as desired.

5. The femoral elevating tool of claim 4, wherein said handle includes a longitudinal slot along which said ball means can be selectively secured to vary the effective distance between said ball means and said bone rest.

6. The femoral elevating tool of claim 4, wherein said bone rest further comprises an upstanding flange attached to said handle, said flange including a single, generally V-shaped tapered cutout to provide a slip-resistant support for a bone to be manipulated by said tool.

7. The femoral elevating tool of claim 4, wherein said ball means includes a generally hemispherical element designed for rotatable interaction with an acetabulum to provide a fulcrum for said tool.

8. The femoral elevating tool of claim 4, wherein said ball means includes a ball element which is removably attached to said tool, whereby said ball portion can be replaced by another ball portion as desired.

9. The femoral elevating tool of claim 4, wherein the distal end of said handle is offset from said proximal end in a direction generally normal to said longitudinal axis.

10. The femoral elevating tool of claim 4, wherein said handle features a relatively thin, ribbon-like profile, and wherein said distal and proximal ends are substantially parallel to one another and offset from one another by a central handle portion which is angularly oriented to both said distal and proximal ends.

11. A femoral elevating tool for use in hip replacement surgical procedures, said tool comprising:
   (a) a handle having proximal, central and distal portions integrally attached along a longitudinal axis of said tool, said distal and proximal portions being substantially parallel to one another and attached to opposite ends of said central portion and offset from one another in a direction generally normal to the longitudinal axis;
   (b) a bone rest attached to said handle adjacent its distal portion, said bone rest including an upstanding flange having a single, generally V-shaped tapered cutout portion;
   (c) ball means for rotatably anchoring said tool in an acetabulum to provide a fulcrum for said tool; and
   (d) means for adjustably mounting said ball means to said handle, whereby said ball means can be selectively secured along said handle to vary the effective longitudinal distance along said axis between said ball means and said bone rest.

12. The femoral elevating tool of claim 11, wherein said ball means comprises a generally hemispherical ball element which is removably attached to said tool, whereby said ball means can be removed and replaced by another ball means as desired.

13. The femoral elevating tool of claim 11, wherein said means for adjustably mounting said ball means includes a longitudinal slot formed in said handle along which said ball means may be selectively secured.

14. The femoral elevating tool for use in hip replacement surgical procedures, said tool comprising a handle having proximal and distal ends and a longitudinal axis along its length, said handle including a bone rest adjacent its distal end, and ball means attached to said handle for anchoring said tool in an acetabulum to provide a fulcrum for said tool, and means for adjusting the longitudinal distance along said handle between said ball means and said bone rest, said adjusting means further comprising a longitudinal slot formed in said handle, wherein said ball means can be selectively secured at a desired position along such slot to thereby adjust the longitudinal distance of said ball means from said bone rest.

15. A femoral elevating tool for use in hip replacement surgical procedures, said tool comprising a handle having proximal and distal ends and a longitudinal axis along its length, said handle including a bone rest adjacent its distal end, ball means attached to said handle for anchoring said tool in an acetabulum to provide a fulcrum for said tool, and means for adjusting the longitudinal distance along said handle between said ball means and said bone rest, said adjusting means further comprising an adjustable mount arrangement of said bone rest and a substantially stationary anchor for said ball means, whereby said bone rest can be selectively attached along said handle at a desirable distance from said ball means.

16. A femoral elevating tool for use in hip replacement surgical procedures, said tool comprising a handle having proximal and distal ends and a longitudinal axis along its length, said handle including a bone rest adjacent its distal end, and ball means attached to said handle for anchoring said tool in an acetabulum to provide a fulcrum for said tool, said ball means further comprising a generally hemispherical element designed for rotatable interaction with an acetabulum to provide a fulcrum for said tool.

17. A femoral elevating tool for use in hip replacement surgical procedures, said tool comprising a handle having proximal and distal ends and a longitudinal axis along its length, said handle including a bone rest adjacent its distal end, and ball means attached to said handle for anchoring said tool in an acetabulum to provide a fulcrum for said tool, said ball means including a portion which is removable from said tool, wherein said removable portion can be replaced by another removable portion as desired.

18. A femoral elevating tool for use in hip replacement surgical procedures, said tool comprising a handle having proximal and distal ends and a longitudinal axis along its length, said handle including a bone rest adjacent its distal end, and ball means attached to said handle for anchoring said tool in an acetabulum to provide a fulcrum for said too, and wherein the distal end of said handle is offset from said proximal end in a direction generally normal to said longitudinal axis.

19. The femoral elevating tool of claim 1, wherein said handle features a relatively thin, ribbon-like profile, and wherein said distal and proximal ends are substantially parallel to one another and are offset from one another by a central handle portion which is angularly oriented to both said distal and proximal ends.

* * * * *

UNITED STATES PATENT AND TRADEMARK OFFICE
CERTIFICATE OF CORRECTION

PATENT NO. : 4,995,875
DATED : February 26, 1991
INVENTOR(S) : Cecil Coes

It is certified that error appears in the above-identified patent and that said Letters Patent is hereby corrected as shown below:

Title page: "19 Claims" should read --20 Claims--. (See attached sheet).

Claim 3 - Column 9 - Line 56 - a comma should be inserted after "V-shaped"

Claim 14 - Column 10 - Line 57 - "The" should be replaced by -- A --

Claim 18 - Column 12 - Line 17 - "too" should be replaced by -- tool --

Claim 19 - Column 12 - Line 20 - "claim 1" should be replaced by -- claim 18 --

Claim 20 is missing from the printed patent. This claim was originally filed as claim 5 and amended in Amendment After Final dated February 21, 1990

20. The femoral elevating tool of claim 14, wherein said ball means is slidably attached along said longitudinal slot by a threaded attachment knob.

Signed and Sealed this

Eighteenth Day of August, 1992

*Attest:*

DOUGLAS B. COMER

*Attesting Officer* — *Acting Commissioner of Patents and Trademarks*

United States Patent [19]

Coes

[11] Patent Number: 4,995,875
[45] Date of Patent: Feb. 26, 1991

[54] FEMORAL ELEVATING TOOL

[76] Inventor: Cecil Coes, 6830 Elwynn Dr., Cincinnati, Ohio 45236

[21] Appl. No.: 199,475

[22] Filed: May 27, 1988

[51] Int. Cl.⁵ .............................................. A61F 2/00
[52] U.S. Cl. ...................................... 606/90; 606/99; 128/20
[58] Field of Search ................... 128/20, 92 R, 92 V, 128/92 VT, 92 VY, 303 R; 623/18, 22, 23; 81/176.2, 94, 98; 606/53, 99, 82, 87, 88, 90

[56] References Cited

U.S. PATENT DOCUMENTS

| | | | |
|---|---|---|---|
| 1,474,497 | 11/1923 | Stolper | 128/20 |
| 2,695,607 | 11/1954 | Hipps et al. | 128/20 |
| 2,863,444 | 12/1958 | Winsten | 128/303 R |
| 3,381,685 | 5/1968 | Von Solbrig | 128/92 VT |
| 3,463,144 | 8/1969 | Hammond | 128/20 |
| 3,467,079 | 9/1969 | James | 128/20 |
| 3,955,568 | 5/1976 | Neufeld | 128/92 VT |
| 4,222,382 | 9/1980 | Antonsson et al. | 128/303 |
| 4,621,619 | 11/1986 | Sharpe | 129/20 |
| 4,632,111 | 12/1986 | Roche | 128/303 |
| 4,642,121 | 2/1987 | Keller | 623/23 |
| 4,686,972 | 8/1987 | Kurland | 128/92 |

OTHER PUBLICATIONS

Richards Reconstructive Systems "Modular Spectron—Design Features and Surgical Technique", Sep., 1986.

Primary Examiner—Robert A. Hafer
Assistant Examiner—Michael Brown
Attorney, Agent, or Firm—Frost & Jacobs

[57] ABSTRACT

A femoral elevating tool for use in hip replacement surgical procedures and preferably including a handle having a longitudinal axis and proximal and distal ends substantially parallel to one another. The proximal and distal ends are preferably offset from one another in a direction normal to the longitudinal axis by a central handle portion. A bone rest adjacent the distal end of the handle preferably includes an upstanding flange having a single, generally V-shaped cutout portion, and a ball for rotatably anchoring the tool in an acetabulum to provide a fulcrum for manipulation of a femur. In a preferred embodiment, the ball is adjustably mounted on the handle to enable selective variation of the effective distance between the ball and the bone rest, and the ball can be removed for cleaning and replacement with a different ball, as appropriate.

20 Claims, 4 Drawing Sheets